United States Patent [19]

Thal et al.

[11] 4,138,489

[45] Feb. 6, 1979

[54] VASODILATING OCTAHYDRO-1,12-METHANO-OXYMETHANO[2,3-A]-INDOLOQUINOLIZINES

[75] Inventors: Claude Thal, Sceaux; Richard Besselievre, Gif sur Yvette; Henri P. Husson, Chevreuse; Pierre Potier, Bois d'Arcy, all of France

[73] Assignee: Agence Nationale de Valorisation de la Recherche (ANVAR), Neuilly-sur-Seine, France

[21] Appl. No.: 700,028

[22] Filed: Jun. 25, 1976

[30] Foreign Application Priority Data

Jun. 25, 1975 [FR] France ................. 75 19960

[51] Int. Cl.² ............... A61K 31/445; C07D 498/06
[52] U.S. Cl. .................... 424/256; 260/244.4; 546/70; 546/48; 546/198; 546/201
[58] Field of Search ............ 260/293.55, 293.53; 424/256

[56] References Cited

U.S. PATENT DOCUMENTS

| 3,536,725 | 10/1970 | Schut | 260/293.53 |
| 3,830,823 | 8/1974 | Castaigne | 260/293.53 |

OTHER PUBLICATIONS

Theilheimer, W., *Synthetic Methods of Organic Chemistry*, vol. 22, S. Karger, New York, 1968, p. 342.

*Primary Examiner*—Henry R. Jiles
*Assistant Examiner*—Richard A. Schwartz
*Attorney, Agent, or Firm*—Michael Klotz

[57] ABSTRACT

Pentacyclic derivatives of the general formula

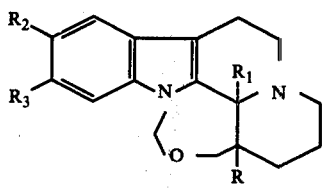

wherein R, $R_1$, $R_2$ and $R_3$ are defined hereinbelow are useful as cerebral protectors and vasodilators.

4 Claims, No Drawings

VASODILATING OCTAHYDRO-1,12-METHANO-OXYMETHANO[2,3-A]-INDOLOQUINOLIZINES

The present invention relates to a pentacyclic derivative of the general formula:

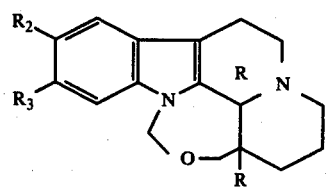

in which:

R represents a hydrogen atom or a hydroxymethyl radical, $R_1$ represents a hydrogen atom.

R and $R_1$ being in the trans position in relation to one another, or alternatively together forming a double bond, and $R_2$ and $R_3$, which may be the same or different, represent a hydrogen atom or a halogen atom or an alkyl radical containing 1 to 4 carbon atoms or alkyloxyl radical whose alkyl part contains 1 to 4 carbon atoms, or else $R_2$ and $R_3$ together form a dioxymethylene radical, its optically active forms, its addition salts with acids, its quaternary ammonium salts and its N-oxides.

The novel products of the present invention have noteworthy therapeutical properties, and are particularly interesting as cerebral protectors and vasodilators. The invention provides a pharmaceutical composition comprising the compounds of this invention.

In another aspect of this invention there is provided two processes for preparing the above pentacyclic derivative; one process related to the production of the derivative having R and $R_1$ in the trans position in relation to one another, the other process relates to the production of the derivative wherein R and $R_1$ together form a double bond.

The invention further provides a process for preparing intermediates for use in the production of the novel compounds of the invention.

Certain alkaloids possessing the eburnane skeleton, such as vincamine and its derivatives, present noteworthy therapeutical properties and are particularly useful for the treatment of cerebral vascular disorders.

The present invention relates to new pentacyclic derivatives possessing a skeleton related to that of eburnane and more particularly of the oxa-E-homoeburnane type, their salts, their preparation and medicinal compositions containing them.

The new products according to the present Invention comply with the general formula:

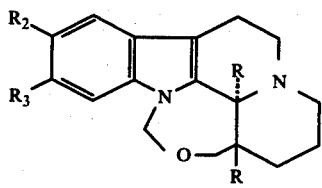

in which:

R represents a hydrogen atom or a hydroxymethyl radical, $R_1$ represents a hydrogen atom it being understood that the symbols R and $R_1$ present the trans configuration in relation to one another, or else R and $R_1$ together form a double bond, and $R_2$ and $R_3$, which may be the same or different, represent a hydrogen atom or halogen atom or an alkyl radical containing 1 to 4 carbon atoms or alkyloxyl radical, the alkyl part of which contains 1 to 4 carbon atoms, or else $R_2$ and $R_3$ together form a methylenedioxy radical.

The present invention also relates to the optical isomers of the products of the general formula (I).

According to the present Invention, the products of the general formula (I) in which R represents a hydrogen atom or a hydroxymethyl radical, the symbols R and $R_1$ being in the trans position in relation to one another, and the symbols $R_2$ and $R_3$ are defined as above, may be obtained by the reduction in an acid medium of an immonium salt of the general formula:

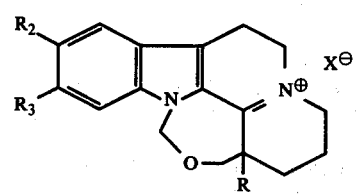

in which R, $R_2$ and $R_3$ are defined as above and X represents an anion such as the perchlorate ion $(ClO_4^-)$.

Generally, the reduction is carried out by means of an alkali borohydride such as sodium borohydride at a pH in the vicinity of 6 in a hydro-alcoholic medium. It is not necessary to isolate the product of the general formula (II) in order to carry out the reduction and it is particularly advantageous to use the immonium salt of the general formula (II) prepared in situ.

Other reducing agents are particularly suitable and among these one may mention: hydrogen in the presence of platinum oxide or carbon containing palladium.

The immonium salt of the general formula (II) may be obtained by the action of formaldehyde on an enamine of the general formula:

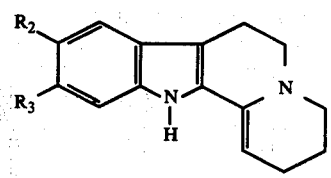

in which $R_2$ and $R_3$ are as defined above, followed by the salification of the product obtained.

Generally speaking, the condensation of the formaldehyde with the enamine of the general formula (III) is carried out in a hydro-alcoholic medium such as a mixture of water/ethanol at a temperature of between 20° C. and the boiling point of the reaction mixture. The salt formation is carried out by the addition of an acid such as perchloric acid, to the reaction medium.

The condensation of the formaldehyde with the enamine of the general formula (III) may lead, according to the relative proportions of formaldehyde and enamine, the temperature and duration of the reaction, either to an immonium salt of the general formula (II) in which R represents a hydrogen atom, or to an immonium salt of the general formula (II) in which R represents a hydroxymethyl radical, or to a mixture thereof. In the latter case, the subsequent reduction leads to a mixture of products of the general formula (I), the constituents of which may be isolated by the application of physicochemical methods such as fractional crystallisation or chromatography.

The immonium salt of the general formula (II) in which R represents a hydroxymethyl radical may also be obtained by the action of formaldehyde on an immonium salt of the general formula (II) in which R represents a hydrogen atom.

The enamine of the general formula (III) may be prepared by the deprotonation in an alkaline medium of an immonium salt of the general formula:

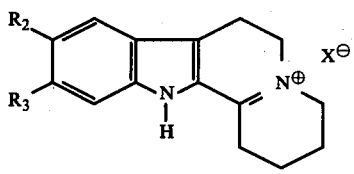

(IV)

in which $R_2$ and $R_3$ are as defined above and X represents an anion such as the perchlorate ion or the chloride ion.

The deprotonation is generally carried out by the addition of an aqueous solution of soda.

The immonium salt of the general formula (IV) may be obtained by the action of phosphorus oxychloride followed by the possible addition of an alkali perchlorate such as sodium perchlorate on to a derivative of a tryptamine of the general formula:

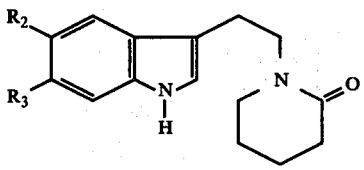

(V)

in which $R_2$ and $R_3$ are as defined above.

The cyclisation with phosphorus oxychloride is carried out in an organic solvent such as benzene, toluene, dichloroethane at a temperature between 20° C. and the reflux temperature of the reaction mixture.

The derivative of tryptamine of the general formula (V) may be obtained by one of the following methods:

(1) by the action of ethyl 5-bromo valerianate on a tryptamine of the general formula:

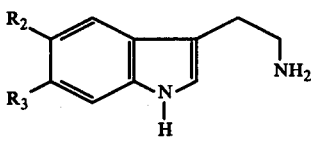

(VI)

in which $R_2$ and $R_3$ are as defined above;

(2) by the action of 1-(4,4-diethoxy-butyl)-2-piperidone on a hydrazine of the general formula:

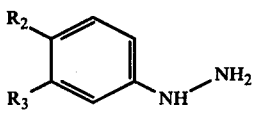

(VII)

in which $R_2$ and $R_3$ are as defined above.

Generally one operates in the presence of zinc chloride at a temperature in the vicinity of 180° C. or in dilute hydrochloric acid at a temperature in the vicinity of 80° C.

The 1-(4,4-diethoxy-butyl)-2-piperidone may be obtained by the action of ethyl 5-bromo valerianate on 4,4-diethoxy butylamine.

The enamine of the general formula (III) may also be prepared by the method of E. WENKERT and B. WICKBERG, J. Amer. Chem. Soc., 84, 4914 (1962) and J. Amer. CHem. Soc., 87, 1580 (1965) or according to the method of R. N. SCHUT and T. J. LEIPZIG, J. Het. Chem., 43 101 (1966) or G. C. MOLINISSON, W. CETENKO, J. SHAVEL, J. Org. Chem., 2771 (1964).

According to the invention, the products of the general formula (I) in which R and $R_1$ together form a double bond may be obtained by the treatment in alkaline medium of an immonium salt of the general formula (II) in which R represents a hydrogen atom.

Generally speaking, the deprotonation is carried out by means of a mineral base such as soda.

The products of the general formula (I) may be separated into their optical isomers by the application of the usual methods. More particularly, one prepares an optically active salt of a product of the general formula (I) which is then separated by fractional crystallisation. The optically active base is regenerated from its salt by using the usual methods. Preferably the splitting is carried out by means of optically active O,O'-di-paratoluoyltartaric acids.

The new products according to the Invention may possibly be purified by physical methods (crystallisation, chromatography) or chemical methods (salt formation, crystallisation of the latter and then decomposition in an alkaline medium).

They may be converted if desired into addition salts with acids, into quaternary ammonium salts or into N-oxides. The salts may be obtained by the action of the new derivatives on acids or reactive esters such as an alkyl halide in suitable solvents. As organic solvents one uses for example alcohols, ethers or chlorinated solvents. The salt formed is precipitated after the concentration of the solution and it is separated by filtration or decantation.

The new products according to the present invention and their salts present noteworthy therepeutical properties. They are particularly interesting as cerebral protectors and vasodilators.

They have been found active in the animal at doses of between 0.1 and 5 mg/kg by intravenous route and at doses of between 5 and 50 mg/kg by oral route.

More particularly:

They increase significantly the survival time of mice placed in a confined atmosphere or at an imaginary altitude.

They reduce the time of reappearance of corticular electrogenesis in the rat subjected to a momentaneous cerebral hypoxia as a result of ischaemia.

They increase the femoral and coronary arterial output in the anaesthetised dog.

They also have a low toxicity. The 50% lethal dose ($DL_{50}$) is generally greater than 200 mg/kg by oral route in the mouse.

For medicinal use, the new compounds are used either in the state of the base, or in the state of acceptable pharmaceutical salts, that is to say ones which are non-toxic at the doses at which they are used.

The following examples, which are given without being restrictive, show how the invention may be put into practice.

In the following, the structure of the products and in particular that of 1,12b trans-1,2,3,4,6,7,12,12b-octahydro-1,1-methanooxymethano(2,3-a) indoloquinolizine, was determined by X-ray analysis and the structure of the other products for which R and $R_1$ each represent a hydrogen atom, was confirmed by the comparison of the spectral data.

EXAMPLE 1

1 g of 2,3,4,6,7,12-hexahydro-(2,3-a) indoloquinolizine is dissolved in 50 mls of ethanol and then one adds 5 mls of a 40% aqueous solution of formaldehyde.

The reaction medium is heated with agitation for 10 minutes at 70° C. One adds 2 mls of perchloric acid and then one adds, in small portions, 2 g of sodium borohydride over 30 minutes.

After addition of 200 mls of water saturated with sodium chloride, one extracts with 200 mls of chloroform. After drying the organic solution over sodium sulphate and evaporating the solvent, one isolates a residue which is filtered in chloroform solution over a column of 80 g of silica.

The elution of the first chloroform fractions (approximately 1 liter ) supplies 1.1 g of 1,12b-trans-1,2,3,4,4,7,12,12b-octahydro-1,12-methanooxymethano-(2,3-a)-indoloquinolizine which, after crystallisation from ethyl acetate melts at 150° C and also possesses the following properties:

Infra-red spectrum: (determination in solution in chloroform).

Bands at 2860–2800 and 2755 cm$^{-1}$ characterising the trans-quinolizidine chain (Bohlmann's banos).

Mass spectrum: peaks at m/e 268 (M$^+$100%) ,267,237.

NMR spectrum: (CDCl$_3$):

4H aromatics between 7.6 and 6.9 ppm; 2H(Na—CH$_2$—O):

2 doublets centered at 5.78 and 4.85 ppm $J_{AB}$ = 12Hz;

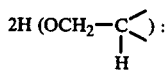

2 quadruplets centered at 3.92 and 3.3 ppm ($J_{AB}$ = 12Hz, $J_{AX}$ = 4Hz, $J_{BX}$ = 10Hz).

The corresponding tartrate is prepared by dissolving 1.1 g of the above base in 40 mls of methanol and then adding 0.3 g. of tartaric acid dissolved in 30 mls of methanol. After concentrating the methanol the salt is precipitated; it is dried and one obtains 1.1 g of 1,12b-trans-1,2,3,4,6,7,12,12b-octahydro-1,12-methanooxymethano-(2,3-a)-indolo-quinolizine-tartrate melting at 222° C. (yield: 79%).

EXAMPLE 2

To a solution of 0.1 g of 2,3,4,6,7,12-hexahydro(2,3-a)indoloquinolizine in 20 mls of ethanol one adds 2 mls of a 40% aqueous solution of formaldehyde.

The reaction mixture is heated, with agitation, at 60° C. for 15 minutes. After concentrating the hydroalcoholic solution one adds 0.1 ml. of perchloric acid. The precipitate which is formed is filtered and then washed with water. In this way one obtains 85 mg of perchlorate which, after alkalisation by a drop of concentrated soda provides 35 mg of 1,12-methanooxymethano-2,3,4,6,7,12-hexahydro(2,3-a)indoloquinolizine which possess the following characteristics:

Mass spectrum: Peaks m/e : 266 (M$^+$100%).

NMR spectrum (CDCl$_3$) 4H aromatics between 7.6 and 6.9 ppm; 2H(Na—CH$_2$—0): 1 singlet at 5.8 ppm; 2H(O—CH$_2$) 1 singlet widened at 4.45 ppm.

EXAMPLE 3

(a) To 1 g of 1,2,3,4,6,7,12H-hexahydro(2,3-a)indoloquinolizinium perchlorate dissolved in 100 mls of ethanol one adds 0.3 g of sodium carbonate and then 25 mls of a 40% aqueous solution of formaldehyde. The reaction mixture is heated for 30 minutes at 60° C. One then adds, after cooling, 200 mls of water and then one extracts with 200 mls of chloroform.

After drying the chloroform solution over sodium sulphate and evaporating the solvent, the residue is dissolved in 100 mls of methanol. One adds over a period of 10 minutes 1 g of sodium borohydride. The state of advancement of the reaction is followed by thin layer chromatography. After the usual treatment one obtains 0.45 g of 1-hydroxymethyl-1,2,3,4,6,7,12,12b octahydro-1,12 methanooxymethano-(2,3-a) indolo-quinolizine which melts at 148° C. and has the following physical properties:

Mass spectrum: peaks at m/e : 298 (M$^+$100%)

NMR spectrum (CDCl$_3$) 4H aromatics between 7.55 and 7 ppm; 2H (Na—CH$_2$O) : 2 doublets centred at 5.88 and 4.99 ppm ($J_{AB}$ = 12Hz); 4H (—O—CH$_2$—C—CH$_2$OH): massif centerd at 3.6 ppm.

(b) The hydrochloride is obtained by dissolving the above compound in the minimum of methanol and adding a few drops of concentrated hydrochloric acid (12N).

The hydrochloride obtained is recrystallised from a mixture of ethyl acetate/methanol (50/50) and melts at 218°–219° C. (c) 1-hydroxymethyl-1,2,3,4,5,6,7,12,12b octahydro-1,12 methanooxymethano-(2,3-a) indoloquinolizine may also be obtained from 2,3,4,6,7,12 hexahydro-(2,3-a) indolo-quinolizine:

To 1 g of 2,3,4,6,7,12 hexahydro-(2,3-a) indoloquinolizine dissolved in 1 ml of ethanol one adds 40 mls of a 40% aqueous solution of formaldehyde. It is agitated for 30 minutes at a temperature of 60° C. It is diluted with 50 mls of methanol and then reduced with 6 g of sodium borohydride. One adds 200 mls of a saturated aqueous solution of sodium chloride and then extracts twice with 200 mls of chloroform.

After the usual treatment one obtains 0.3 g of 1-hydroxymethyl-1,2,3,4,6,7,12,12b-octahydro-1,12 methanooxymethano-(2,3-a) indolo-quinolizine which is identical to the product obtained in Example 3a.

EXAMPLE 3a.

One heats to 60° C. a solution of 4.6 g of 10-methoxy-2,3,4,6,7,12-hexahydro-(2,3-a) indolo-quinolizine in 460 mls of ethanol and then one adds over a period of 1 minute under an atmosphere of nitrogen 9 mls of a 30% aqueous solution of formaldehyde. It is left for exactly 10 minutes in contact at 65° C., and then one adds 2.39 mls of 70% perchloric acid and it is cooled to 20° C. in a bath of iced water. One then adds in small portions 3.15 g of sodium borohydride and it is left with agitation for 45 minutes. After diluting with 180 mls of a saturated solution of sodium chloride and 800 mls of water, one extracts three times with 250 mls of dichloromethane, the organic phase is washed twice with 100 mls of water, dried over sodium sulphate, filtered and concentrated to dryness under reduced pressure (20 mm of mercury) at 20° C. The residue is taken up in three times 200 mls of boiling isopropyl oxide; the solution obtained after elimination of a brown residue by filtration is concentrated to a volume of 150 mls. After cooling for 1 hour to +4° C. the crystals are filtered and dried under reduced pressure (20 mm of mercury) at 20° C. In this way one obtains 3.5 g of 1,12b trans-10-methoxy-1,2,3,4,6,7,12,12b-octahydro-1,12 methanooxymethano-(2,3-a) indolo-quinolizine melting at 136° C.

After recrystallisation from a mixture of acetone and water (½ by volume), the product melts at 140° C.

Analysis % Calc.: C, 72.46; H, 7.43; N, 9.39; O, 10.72. Found: C, 71.6; H, 7.25; N, 9.15; O, 11.5.

10-methoxy-2,3,4,6,7,12-hexahydro-(2,3-a) indolo-quinolizine may be prepared in the following manner:

To a solution of 5.44 g of 1-[2(6-methoxy-3-indolyl) ethyl]-2-piperidone in 300 mls of 1,2-dichloroethane one adds, under an atmosphere of nitrogen and accompanied by agitation, over a period of 10 minutes 5 mls of phosphorus oxychloride. It is then heated under reflux for 3 hours and then allowed to return to a temperature of 50° C. One then adds 150 mls of distilled water and heats it again under reflux for 45 minutes. After cooling to 50° C, the reaction mixture is decanted. The organic phase is extracted with twice 20 mls of water at approximately 50°. To the aqueous phase one adds 6 g of sodium perchlorate.

After cooling for 1 hour to 4° C, the precipitate is separated by filtration and then dried under reduced pressure (0.5 mm of mercury), at 20° C.

In this way one obtains 6.5 g of 10-methoxy-1,2,3,4,6,7,12H-hexahydro(2,3-a)-indolo-quinolizinium perchlorate in the form of a light green crystalline solid.

This product is dissolved in 400 mls of boiling methanol. One adds 400 mls of distilled water and leaves it to cool to 20° C. One then adds drop to drop, accompanied by agitation, 2 mls of 10N soda so as to obtain a pH in the vicinity of 10. The mixture is cooled in an ice bath. After cooling for 1 hour, the product obtained is separated by filtration and then dried under reduced pressure (0.55 mm of mercury) at 20° C. In this way one obtains 4.6 g of 10-methoxy-2,3,4,6,7,12-hexahydro-(2,3-a)-indoloquinolizine melting at 166° C.

1-[2(6-methoxy-3-indolyl)-ethyl]-2-piperidone may be prepared in the following manner:

One heats under a reflux, under an atmosphere of nitrogen, a suspension of 9.5 g of 6-methoxy tryptamine and 5.32 g of sodium carbonate in 124 mls of methoxyethanol and then one adds over a period of 30 hours accompanied by agitation a solution of 10.4 g of ethyl bromovalerianate in 82 mls of methoxyethanol. The agitation and the reflux are continued for 1 hour and 30 minutes after the end of the addition and the mixture is concentrated under reduced pressure (0.5 mm of mercury) down to a volume of 50 mls. After dilution with 500 mls of distilled water, one extracts with three times 200 mls of dichloromethane. The organic phase is washed with two times 100 mls of a normal solution of hydrochloric acid and two times 100 mls of a saturated solution of sodium chloride. After drying over magnesium sulphate, treatment with animal charcoal and filtration, it is concentrated to dryness under reduced pressure (20 mm of mercury) at 20° C. One obtains in this way 11.2 g of a light yellow solid which is purified by chromatograhy on a column of 150 g of silica gel (neutral pH 0.05 - 0.2) contained in a column 1.6 cm in diameter. It is eluted successively with 300 mls of a mixture of cyclohexane/ethyl acetate (50:50 by volume), 300 mls of a mixture of cyclohexane/ethyl acetate (25:75 by volume), 600 mls of ethyl acetate and 1200 mls of a mixture of ethyl acetate/methanol (98:2 by volume), collecting fractions of 100 mls. Fractions 7 to 25 are combined and concentrated to dryness under reduced pressure (20 mm of mercury) at 20° C. One obtains in this way 7.5 g of 1-[2(6-methoxy-3-indolyl)ethyl]-2-piperidone melting at 146° C.

6-methoxytryptamine may be prepared according to N.N. SUVOROV and co-workers, Zh, Obshch. Khim., 30, No. 9, 3118 (1960).

EXAMPLE 5

One dissolves 18.5 g of 10-fluoro-2,3,4,6,7,12-hexahydro-(2,3-a)-indolo-quinolizine in 2 liters of ethanol at 60° C. One adds in one go 49.2 mls of formaldehyde in a 30% aqueous solution. The reaction mixture is agitated for 10 minutes at 60° C. One adds 12.9 mls of 65% perchloric acid and the reaction mixture is cooled to 20° C. One then adds 15.9 g of sodium borohydride and it is left with agitation for 1 hour and 20 minutes. One then pours the reaction mixture into 800 mls of a saturated aqueous solution of sodium chloride. It is agitated for 45 minutes with 800 mls of methylene chloride and then the organic phase is separated. The aqueous phase is extracted three times with 800 mls of methylene chloride. The organic extracts are combined, washed with 500 mls of distilled water and dried over sodium sulphate in the presence of 5 g of bleaching carbon. After filtration and concentration to dryness under reduced pressure (20 mm of mercury) one obtains 21.2 g of a residue which is dissolved in 80 mls of methylene chloride and filtered over 70 g of silica contained in a column 2.5 cm in diameter. The silica is washed with 1.7 liters of methylene chloride. The methylene chloride is concentrated under reduced pressure (20 mm of mercury): one obtains 15.9 g of a crystalline residue which is purified by recrystallisation from 930 mls of isopropyl oxide. One obtains in this way 8.5 g of 1,12b-trans-1-fluoro-1,2,4,6,7,12,12b-octahydro-1,12-methanoxymethoano-(2,3- a)-indolo-quinolizine melting at 158°–159° C.

Analysis Calculated %: C, 71.31; H, 6.69; F, 6.63; N, 9.78. Found: C, 71.40; H, 6.65; F, 6.75; N, 9.60.

10-fluoro-2,3,4,6,7,12-hexahydro-(2,3-a)-indolo-quinolizine may be prepared in the following manner:

To a suspension of 24 g of 1-[2(6-fluoro-3-indolyl)-ethyl]-piperidone in 1 liter of toluene one adds over a period of 30 minutes 24 mls of phosphorus oxychloride dissolved in 100 mls of toluene. It is then heated to 80° C. for 3 hours. It is then left to cool and one adds, accompanied by agitation, 550 mls of distilled water. It is heated again to 80° C. for 45 minutes. It is allowed to cool to 50° C. and the aqueous phase is separated by decantation. One extracts the organic phase with twice 100 mls of water. One adds, accompanied by agitation, 24 g of sodium perchlorate dissolved in 240 mls of distilled water, to the combined aqueous extracts. A product is precipitated. After 1 hour and half of cooling to 4° C., the crystals are separated by filtration. In this way one obtains 30.4 g of 10-fluoro-1,2,3,4,6,7,12H-hexahydro-(2,3-a)-indolo-quinolizinium perchlorate melting at 223° C.

30.3 go of the perchlorate thus obtained is dissolved in 2.1 liters of boiling methanol and then one adds 2.1 liters of distilled water and one cools to a temperature in the vicinity of 20° C. One then adds 100 mls of normal soda. A product is precipitated, which is separated by filtration, washed with 500 mls of distilled water.

In this way one obtains 17.2 g of 10-fluoro-2,3,4,6,7,12-hexahydro-(2,3-a)-indolo-quinolizine melting at 134° C.

1[2(6-fluoro-3-indolyl)ethyl)] piperidone may be prepared in the following manner:

To 22.7 g of 6-fluoro tryptamine dissolved in 600 mls of methoxyethanol one adds 13.3 g of anhydrous sodium carbonate and one heats under reflux under an atmosphere of nitrogen. One adds, over a period of 3 days, 26.5 g of ethyl 5-bromo valerianate in 50 mls of methoxyethanol. The reflux is continued for 5 hours. After the end of the addition one concentrates to dryness under reduced pressure (20 mm of mercury). The residue is taken up in 300 mls of water. It is extracted 4 times with 450 mls of methylene chloride. The organic extracts are combined and are washed with 100 mls of N hydrochloric acid and then with twice 100 mls of water, dried over sodium sulphate in the presence of 0.2 g of bleaching carbon. After filtration and concentration to dryness under reduced pressure (20 mm of mercury), one obtains 27.7 g of a crystalline residue which is purified by chromatography over 125 g of silica contained in a column with a diameter of 3 cm, by eluting with 3.5 liters of ethyl acetate. After the concentration of the eluates one obtains 24 g of 1-[2(6-fluoro-3-indolyl)ethyl] piperidone melting at 146 C. 6-fluoro tryptamine may be prepared according to the process described in British Pat. No. 846.675.

EXAMPLE 6

One heats to 60° C. a suspension of 8.6 g of 9-methyl-2,3,4,6,7,12-hexahydro-(2,3-a)-indolo-quinolizine in 750 mls of ethanol. One obtains a solution to which one adds, over a period of 2 minutes, 20.6 mls of a 30% aqueous solution of formaldehyde. The reaction mixture is maintained at 60° C. for 10 minutes. One adds 5.4 mls of 70% perchloric acid over a period of 1 minute and the reaction medium is then cooled to 20°C. One then adds in small portions and accompanied with agitation 7.1 g of sodium borohydride over a period of 15 minutes, it is allowed to continue with agitation for a further 30 minutes and then the mixture is poured into 375 mls of a saturated solution of sodium chloride, it is left for 5 minutes with agitation and extracted twice with 400 mls of chloroform. The organic phase is dried, filtered over bleaching carbon and evaporated to dryness under reduced pressure (20 mm of mercury). In this way one obtains 9.8 g of crude product which is chromatographed over 500 g of basic alumina contained in a column with a diameter of 43 cm, eluting with methylene chloride and collecting fractions of 120 mls. Fractions 2 to 14, after concentration, provide 5 g of a product which is recrystallised from 50 mls of acetone. One obtains in this way 3.3 g of 1,12b-trans-9-methyl-1,2,3,4,6,7,12,12b-octahydro-1,12-methanoxymethano-(2,3-a)-indolo-quinolizine, melting at 183° C.

Analysis Calculated %: C, 76.56; h, 7.85; N, 9.91. Found: 76.5; H, 7.6; N, 9.7. 9-methyl-2,3,4,6,7,12-hexahydro-(2,3-a)-indolo-quinolizine may be prepared in the following manner:

To a solution of 16 g of 1-[2(5-methyl-3-indolyl)-ethyl]-2-piperidone in 450 mls of toluene one adds 15 mls of phosphorus oxychloride and heats the mixture at 85° C. for 3 hours. It is cooled to 20° C. and then one adds 200 mls of water and heats it again to 90° C. for 40 minutes accompanied by agitation. The mixture is cooled. After decantation, the organic phase is washed with 200 mls of water. The aqueous phases are combined and heated to 40° C. One then adds over a period of 3 minutes a solution of 15 g of sodium perchlorate in 100 mls of water. An oil is salted out. After cooling, the crystallised yellow product is separated by filtration and dried. One obtains in this way 13.1 g of 9-methyl-1,2,3,4,6,7,12H-hexahydro-(2,3-a)indolo-quinolizinium perchlorate in the form of yellow crystals. of 750 mls of water and 750 mls of methanol and one adds 4N soda to it to bring the pH to 20. An emulsion is formed which crystallises when cooled. After leaving it for 1 hour at 5° C., it is filtered. One obtains in this way 8.6 g of 9-methyl-2,3,4,6,7,12 hexahydro-(2,3-a)indolo-quinolizine melting at 167° C.

1-[2(5-methyl-3-indolyl)-ethyl]-2-piperidone may be prepared in the following manner:

To a suspension of 14 g of 5-methyl tryptamine hydrochloride and 7.2 g of sodium carbonate in 250 mls of methoxyethanol heated under a reflux, one adds over a period of 8 hours a solution of 15 g of ethyl 5-bromo valerianate in 45 mls of methoxyethanol. The heating under a reflux is maintained for a further 16 hours. After cooling, the mineral salts in suspension are separated by filtration and the filtrate is evaporated to dryness under reduced pressure (20 mm of mercury). The residue is taken up in a mixture of 250 mls of water and 500 mls of methylene chloride. After decanting, the aqueous phase is extracted again with 250 mls of methylene chloride. The combined organic phases are washed 3 times with 500 mls of dilute hydrochloric acid, dried over sodium sulphate, filtered over bleaching carbon and evaporated to dryness under reduced pressure. In this way one obtains 16 g of 1-[2(5-methyl-3-indolyl)]ethyl 2-piperidone in a form which can be used without subsequent purification. 5-methyl tryptamine hydrochloride may be prepared according to M. PROTIVA and co-workers, Czech. Chem. Comm., 25, 784 (1960).

EXAMPLE 7

One heats to 60° C. a solution of 8.4 g of 9-methoxy-2,3,4,6,7,12-hexahydro(2,3-a) indolo-quinolizine in 840 mls of ethanol and one rapidly adds 22.2 mls of a 30% aqueous solution of formaldehyde. The temperature is maintained for 10 minutes at 60° C. and then one rapidly adds 5.6 mls of 70% perchloric acid. The reaction medium is cooled to 20° C. and becomes heterogeneous. One adds in small portions over a period of 4 minutes 7.20 g of sodium borohydride and then one leaves it for 45 minutes with agitation, one adds 300 mls of a saturated solution chloride and agitates for 10 minutes. One then adds 1000 mls of water and 1000 mls of methylene chloride and continues the agitation for a further 10 minutes. After decanting, the aqueous phase is extracted again with 1000 mls of methylene chloride. These organic phases are combined, washed with 500 mls of water and 750 mls of a saturated solution of sodium bicarbonate and dried over sodium sulphate, filtered over bleaching charcoal. In this way one obtains, after evaporation to dryness under reduced pressure (20 mm of mercury) 11 g of crude product which is chromatographed over 200 of basic alumina contained in a column with a diameter of 30 cm, eluting with methylene chloride and collected fractions of 60 mls. Fractions 2 to 24 after concentration provide 7.7 g of a product which is recrystallised from 150 mls of a mixture of ethyl acetate and isopropyl oxide (1:1 by volume). One obtains in this way 5 g of 1,12b-trans-9-methoxy-1,2,3,4,6,7,12,12b octahydro-1,12 methanoxymethano(2,3-a) indolo-quinolizine melting at 130° C.

Analysis Calculated: C, 72.46; H, 7.43; N, 9.39. Found: C, 72.4; H, 7.4; N, 9.2.

9-methoxy-2,3,4,6,7,12-hexahydro (2,3-a) indolo-quinolizine may be prepared in the following manner:

To a suspension of 17 g of 1[2(9-methoxy-3-indolyl)-]ethyl-2-piperidone in 500 mls of toluene one adds over a period of 2 minutes 17.2 mls of phosphorus oxychloride and then one heats to 80° C. for 3 hours accompanied by agitation. It is cooled to 50° C. and then one adds 400 mls of water and heats the mixture again to 85° C. for 30 minutes. After cooling, one adds 1000 mls of water, decants and eliminates the organic phase. To the aqueous phase, heated to 50° C., one adds a solution of 17 g of sodium perchlorate in 180 mls of water. A precipitate is formed which, after cooling to 20° C., is separated by filtration. In this way one obtains 18 g of 1,2,3,4,6,7,12H hexahydro-(2,3-a) indolo quinolizinium perchlorate in the form of pale yellow crystals. One dissolves 16.5 g of the perchlorate so obtained in a mixture of 1300 mls of methanol and 1500 mls of water at 55° C. It is cooled to 40° C. and one adds over a period of 10 minutes 100 mls of 4N soda. After 30 minutes of cooling to 10° C., the crystals obtained are separated by filtration. One obtains in this way 8.5 g of 9-methoxy-2,3,4,6,7,12hexahydro (2,3-a) indole-quinolizine in the form of yellow crystals melting at about 130° C.

1-[2(5-methoxy-3-indolyl)-ethyl]-2-piperidone may be prepared in the following manner:

One heats to 80° C. a solution consisting of 140 mls of water, 60 mls of acetic acid and 40 mls of normal hydrochloric acid. One then adds 5.52 g of p-methoxyphenylhydrazine followed by 9.7 g of 1-(4,4-diethoxybutyl)-2-piperidone. The solution is maintained at 80° C. for 2 hours. It is then cooled to 5° C. and then one adds 200 mls of water and 150 mls of methylene chloride. After decanting, the aqueous phase is extracted again with 200 mls of methylene chloride. The organic phases are combined, washed with 100 mls of water and then with a saturated solution of sodium bicarbonate, dried over sodium sulphate, filtered over bleaching charcoal and then evaporated to dryness under reduced pressure (20 mm of mercury). The residue (10 g ) is chromatographed over 75 g of silica gel contained in a column with a diameter of 2.7 cm and eluting with ethyl acetate, collecting fractions of 120 mls. Fractions 4 to 12 are evaporated. In this way one obtains 7.5 g of 1[1(5-methoxy-3-indolyl)-ethyl]2-piperidone melting at 150° C. 1-(4,4-diethoxy-butyl)-2-piperidone may be prepared in the following manner:

To a solution of 97 g of 4,4-diethoxybutylamine in 1800 mls of methoxy -ethanol heated under a reflux one adds over a period of 19 hours a solution of 130 g of ethyl 5-bromo valerianate in 160 mls of methoxyethanol. The mixture is heated under a reflux for a further hour after the end of the addition. After cooling, the mineral salts are separated by filtration and the filtrate is evaporated to dryness under reduced pressure (20 mm of mercury). The residue is dissolved in 1000 mls of methylene chloride, washed twice with 500 mls of water and then with 500 mls of a 4% solution of citric acid. The organic phase is dried over sodium sulphate, filtered over bleaching charcoal and evaporated to dryness. In this way one obtains 122.5 g of crude 1-(4,4-diethoxy-butyl)-2-piperidone which is used without subsequent purification.

EXAMPLE 8

To a solution of 17.5 g of 9-chloro-2,3,4,6,7,12-hexahydro(2,3-a)-indolo-quinolizine in 1700 mls of ethanol at 60° C. one rapidly adds 45.4 mls of a 30% aqueous solution of formaldehyde. It is maintained at 60° C. for 10 minutes and then one rapidly adds 11.5 mls of 70% perchloric acid. After cooling the mixture to 20° C. one adds, over a period of 3 minutes in small portions, 14.7 g of sodium borohydride accompanied by agitation. The agitation is continued for a further 30 minutes and then one adds 350 mls of a saturated solution of sodium chloride and 500 mls of water. The agitation is continued for a further 20 minutes and then it is extracted with 800 mls of methylene chloride. The organic layer is washed with 1000 mls of water, dried over sodium sulphate, filtered over bleaching charcoal and evaporated to dryness. One obtains 20 g of a crude product which is recrystallised from 150 mls of ethyl acetate. One obtains in this way 11 g of 1,12b trans-9-chloro-1,2,3,4,6,7,12,12b octahydro-1,12 methanoxymethano-(2,3-a) indolo-quinolizine in the form of white crystals melting at 154° C.

Analysis Calculated %: C, 67.43; H, 6.33; Cl, 11.71; N, 9.25. Found: C, 67.6; H, 6.3; Cl, 11.8; N, 9.0. 9-chloro-2,3,4,6,7,12 hexahydro (2,3-a) indolo-quinolizine may be prepared in the following manner:

To a suspension of 16.5 g of 1-[2(5-chloro-3-indolyl)-ethyl]-2-piperidone in 375 mls of toluene one adds 16.5 mls of phosphorus oxychloride and then one heats this mixture for 3 hours at 80° C. After cooling to 30° C. one adds 750 mls of water and then one heats again at 85° C. for 1 hour. After cooling and decanting, the organic phase is extracted with 100 mls of water. The aqueous phases are combined and heated to 55° C., one then adds a solution of 16.5 g of sodium perchlorate in 180 mls of water. The suspension formed is cooled to 15° C. and then filtered. One obtains in this way 21 g of 9-chloro-1,2,3,4,6,7,12-H hexahydro(2,3-a) indolo-quinolizinium perchlorate in the form of orange crystals melting at about 300° C. with decomposition.

One dissolves 28 g of the perchlorate thus obtained in a mixture brought to reflux of 850 mls of methanol and 500 mls of water. One then adds 35 mls of 4N soda whilst slowly cooling to 5° C. The crystals formed are separated by filtration and dried. One obtains in this way 17.5 g of 9-chloro-2,3,4,6,7,12 hexahydro(2,3-a) indolo-quinolizine in the form of yellow crystals melting at 147° C.

1-[2(5-chloro-3-indolyl) ethyl]-2-piperidone may be prepared in the following manner:

One gradually heats a mixture of 31 g of anhydrous zinc chloride, 31 g of p-chlorophenylhydrazine and 52.5 g of 1-(4,4-diethoxy-butyl)-2-piperidone to 115° C. The ethanol formed is eliminated by distillation. One continues heating, and at 170° C. an exothermic reaction is formed which brings the mixture to 240° C. The mixture is then maintained at 180° C. for 4 hours.

After cooling the mixture, one adds 150 mls of a 2N solution of acetic acid and then heats under a reflux for 5 minutes. After cooling, one adds 150 mls of methylene chloride. After decanting, the aqueous phase is extracted again with 200 mls of methylene chloride. The organic phases are combined, washed with 200 mls of water, 300 mls of a saturated solution of sodium bicarbonate, dried over sodium sulphate and evaporated to dryness under reduced pressure (20 mm of mercury). The residue (56 g) is chromatographed over 500 g of silica gel contained in a column 5 cm in diameter and eluting with ethyl acetate, collecting fractions of 400 mls. Fractions 8 to 15 are evaporated to dryness. One obtains in this way 32 g of 1-[2(5-chloro-3-indolyl) ethyl]-2-piperidone, melting at 158° C.

EXAMPLE 9

To a solution heated to 60° C. of 19 g of 9-fluoro-2,3,4,6,7,12 hexahydro-(2,3-a) indolo-quinolizine in 1900 mls of ethanol one adds, over a period of 1 minute, 40.5 mls of a 30% aqueous solution of formaldehyde. It is left at 60° for 10 minutes whilst agitating and then one adds, over a period of 1 minute, 10.8 mls of a 70% perchloric acid solution. It is cooled to 20° and then one adds in small fractions 14.3 g of sodium borohydride, and it is then left for a further 30 minutes accompanied by agitation. One then adds 600 mls of a saturated solution of sodium chloride and then extracts it with twice 1000 mls of chloroform. The combined extracts are washed with 1000 mls of water, dried over sodium sulphate, filtered and evaporated to dryness under reduced pressure (20 mm of mercury). The residue (22.5 g) is recrystallised twice from acetone. One obtains in this way 7.3 g of 1,12b-trans-9-fluoro-1,2,3,4,6,7,12,12b octahydro-1,12 methanoxymethano-(2,3-a) indolo-quinolizine in the form of pale yellow crystals melting at about 155° C.

Analysis Calculated %: C, 71.31; H, 6.69; F, 6.63; N, 9.78. Found: C, 70.3; H, 6.5; F, 6.9; N, 9.8.

9-fluoro-2,3,4,6,7,12-hexahydro (2,3-a) indolo-quinolizine may be prepared in the following manner:

To a suspension of 30 g of 1-[2(5-fluoro-3-indolyl)-]ethyl-2-piperidone in 1500 mls of toluene, one adds 28 mls of phosphorus oxychloride and heats to 80° C., accompanied by agitation, for 3 hours. It is then cooled to about 50° C. and then one adds 750 mls of water and heats to 85° C. for 45 minutes. After cooling and decanting, the organic phase is extracted twice with 100 mls of water, the aqueous phases are combined and heated to 50° C. One then adds a hot solution of 30 g of sodium perchlorate in 200 mls of water. A precipitate is formed. The suspension is agitated for 30 minutes in an ice bath. The precipitate is separated by filtration. In this way one obtains 40 g of 9-fluoro-1,2,3,4,6,7,12-H hexahydro(2,3-a) indolo-quinolizinium perchlorate in the form of orange crystals.

This perchlorate is dissolved at 20° C. in a mixture of 2500 mls of methanol and 2500 mls of water. One adds, with agitation, to this solution 10N soda so as to bring the pH to 10. A precipitate is formed. The mixture is agitated for 30 minutes in an ice bath. The precipitate is separated by filtration and dried and one obtains in this way 19 g of 9-fluoro-2,3,4,6,7,12 hexahydro(2,3-a) indolo-quinolizine in the form of orange crystals melting at about 108° C.

1-[2(5-fluoro-3-indolyl)]ethyl-2-piperidone can be prepared in the following manner:

One gradually heats a mixture of 16.3 g of anhydrous zinc chloride, 14.5 g of p-fluorophenylhydrazine and 28 g of 1-(4,4-diethoxy-butyl)-2-piperidone. At 110° C. one eliminates by distillation the ethanol formed and then one continues to heat. From 150° C., an exothermic reaction is produced and the temperature of the reaction mixture rises to a temperature of 210° C. The temperature is then maintained at 180° C. for 4 hours. After cooling to about 100° C., it is extracted twice under a reflux with 100 mls of a water/ethanol mixture (1:1 by volume). To these extracts one adds 10 mls of acetic acid and then one extracts three times with 200 mls of methylene chloride. The combined organic extracts are washed with 200 mls of a saturated solution of sodium bicarbonate, dried over sodium sulphate, filtered over a bleaching charcoal and evaporated to dryness, (20 mm of mercury). One obtains 38 g of a brown gum which is chromatographed over 500 g of silica gel contained in a column with a diameter of 5 cm, collecting fractions of 500 mls and eluting with ethyl acetate. Fractions 20 to 36 are combined and evaporated to dryness. In this way one obtains 22 g of 1-[2(5-fluoro-3-indolyl) ethyl]-2-piperidone in the form of pale yellow crystals melting at 152° C.

EXAMPLE 10

One heats to 65° C. under an atmosphere of nitrogen a solution of 17.8 g of 9,10-dioxymethylene-2,3,4,6,7,12 hexahydro(2,3-a) indolo-quinolizine in 1700 mls of ethanol, and then in a period of 1 minute one adds 37.6 mls of a 30% aqueous solution of formaldehyde. A precipitate is formed. It is maintained at 65° C. for 10 minutes and then in a period of 1 minute one adds 9.9 mls of 70% perchloric acid and then leaves it to cool with agitation to 25° C. One then adds over a period of 15 minutes, in small portions, 13.2 g of sodium borohydride and then continues the agitation for 30 minutes. One adds to the mixture 700 mls of a saturated solution of sodium chloride, 1000 mls of chloroform and 400 mls of water. After decanting, the aqeuous phase is extracted again with 600 mls of chloroform. The organic fractions are combined, washed twice with 1500 mls of water, dried over sodium sulphate and concentrated to dryness. The residue (16.8 g) is chromatographed ober 400 g of silica gel contained in a column with a diameter of 5 cm, collecting fractions of 600 mls and eluting with a mixture of methylene chloride/ethyl acetate (85:15 by volume). Fractions 5 to 15 are combined and evaporated. The residue, 8.9 g, is recrystallised successively from a mixture of ethyl acetate and acetone. In this way one obtains 3.5 g of 1,12b-trans-9,10-methylenedioxy-1,12-methanoxymethano-1,2,3,4,6,7,12,12b octahydro(2,3-a) indolo-quinolizine in the form of white crystals melting at 234° C.

Analysis Calculated %: C, 69.21; H, 6.45; N, 8.97; O, 15.37. Found: C, 69.4; H, 6.5; N, 8.8; o, 15.3. 9,10-methylenedioxy-2,3,4,6,7,12-hexahydro(2,3-a) indolo-quinolizine may be prepared in the following manner:

One heats under a reflux under an atmosphere of nitrogen a solution of 10.25 g of [2(5,6-methylenedioxy-3-indolyl) ethyl]-2-piperidone in 475 mls of 1,2-dichloroethane and one adds over a period of 10 minutes a solution of 10.5 mls of phosphorus oxychloride in 25 mls of 1,2-dichloroethane.

It is maintained for a further 3 hours under reflux. After cooling to about 50° C., one adds 250 mls of water and then one heats it again under a reflux for 45 minutes. After cooling and decanting one extracts the organic phase with 50 mls of water; the aqueous phases are combined and heated to 50° C. One then adds a solution of 10.25 g of sodium perchlorate in 50 mls of distilled water. A precipitate is formed. After cooling for 30 minutes the precipitate is separated by filtration and dried. It is filtered and in this way one obtains 12.2 g of methylene-9,10-dioxy-1,2,3,4,6,7,12H-hexahydro(2,3-a) indolo-quinolizinium perchlorate in the form of dark green crystals.

This perchlorate is dissolved under an atmosphere of nitrogen under a reflux in a mixture of 750 mls of methanol and 500 mls of water. It is cooled to 45° C. and then one adds 25 mls of 4N soda. A precipitate is formed. This mixture is cooled in an ice bath for 2 hours. The precipitate is separated by filtration and then dried. In this way one obtains 8.5 g of methylene-9,10-dioxy-2,3,4,6,7,12-hexahydro(2,3-a) indolo-quinolizine in the form of a green solid melting at about 180° C.

1-[2(methylene-5,6-dioxy-3-indolyl) ethyl]-2-piperidone may be prepared in the following manner:

One heats under a reflux a solution of 22 g of methylene-3,4-dioxyphenylhydrazine hydrochloride in 880 mls of a mixture of ethanol and water (50:50 by volume) and 200 mls of 5N hydrochloric acid. One then adds over a period of 5 minutes a solution of 28.4 g of 1-(4,4-diethoxybutyl)-2-piperidone in 140 mls of ethanol, heats it again under a reflux for 5 minutes. After cooling, the solution is neutralised by the addition of 100 mls of a saturated solution of potassium bicarbonate. It is then extracted successively with 500, 350 and 350 mls of methylene chloride. The organic phases are combined, washed with 200 mls of water, dried over sodium sulphate, filtered over bleaching charcoal and evaporated to dryness under reduced pressure (20 mm of mercury). The residue (34 g) is chromatographed over 500 g of silica contained in a column with a diameter of 5 cm, collecting fractions of 500 mls and eluting with ethyl acetate. Fractions 11 to 18 are combined and evaporated. In this way one obtains 11.75 g of 1-[2(methylene-5,6-dioxy-3-indolyl) ethyl]-2-piperidone melting at 180° C.

EXAMPLE 11

One heats to 65° C. a solution of 7.3 g of 9,10-dimethoxy-2,3,4,6,7,12-hexahydro (2,3-a) indolo-quinolizine in 730 mls of ethanol. One adds, over a period of 1 minute, 14.4 mls of a 30% aqueous solution of formaldehyde. It is then left at 65° C. for 10 minutes and then one adds in a single go 3.8 mls of 70% perchloric acid. After cooling to 20° C., one adds in small portions 4.9 g of sodium borohydride and then leaves it with agitation for 30 minutes. One adds 300 mls of a saturated solution of sodium chloride and 600 mls of methylene chloride. After decanting, the aqueous phase is extracted with 300 mls of methylene chloride. The organic phases are combined, washed twice with 500 mls of water, dried over magnesium sulphate and evaporated to dryness under reduced pressure (20 mm of mercury). The residue (8.3 g) is chromatographed over 350 g of basic alumina contained in a column of 3.8 cm diameter, collecting fractions of 300 mls and eluting with methylene chloride. Fractions 6 to 14 are combined and evaporated to dryness. The residue (5 g) recrystallised from 100 mls of ethyl acetate. One obtains in this way 3.5 g of 1,12b-trans-9,10-dimethoxy-1,12-methanoxymethano-1,2,3,4,6,7,12,12b-octahydro(2,3-a) indolo-quinolizine in the form of yellow crystals melting at 170° C.

Analysis Calculated: C, 69.49; H, 7.37; N, 8.53; 14.61. Found: C, —69.0; H, 6.8; N, 8.4; O, 14.9.

9,10-dimethoxy-2,3,4,6,7,12-hexahydro (2,3-a) indolo-quinolizine may be prepared in the following manner:

One heats under a reflux for 3 hours a solution of 14 g of 1-[2(5,6-dimethoxy-3-indolyl) ethyl]-2-piperidone and 11.7 mls of phosphorus oxychloride in 700 mls of 1,2-dichloroethane.

After cooling to 50° C., one adds 350 mls of water and heats for 45 minutes under a reflux. After cooling and decanting, the organic phase is extracted twice with 50 mls of water. The combined aqueous phases are heated to 50° C.; one then adds a lukewarm solution of 14 g of sodium perchlorate in 70 mls of water. A precipitate is formed. The suspension is cooled for 1 hour in an ice bath. The crystals are separated by filtration and dried. One obtains 13.7 g of 9,10-dimethoxy-1,2,3,4,6,7,12H-hexahydro (2,3-a) indolo-quinolizinium perchlorate in the form of green crystals.

This perchlorate (13.5 g) is dissolved under a reflux in a mixture of water and methanol (50:50 by volume). After cooling to 50° C. one adds, drop by drop, 10N soda so as to bring the pH to 10. A precipitate is formed. The suspension is maintained for 1 hour in an ice bath and then the precipitate is separated by filtration and dried. One obtains in this way 7.4 g of 9,10-dimethoxy-2,3,4,6,7,12-hexahydro (2,3-a) indolo-quinolizine in the form of a yellow solid melting at 122° C. 1-[2(5,6-dimethoxy-3-indolyl) ethyl]-2-piperidone may be prepared in the following manner:

One dissolves 54 g of 3,4-dimethoxy phenylhydrazine hydrochloride in a mixture of 750 mls of ethanol, 750 mls of water and 350 mls of 5% hydrochloric acid. It is heated under a reflux, and then one adds over a period of 5 minutes a solution of 63 g of 1-(4,4-diethoxybutyl)-2-piperidone in 250 mls of ethanol. After heating under a reflux for 2 hours and then cooling, one eliminates the ethanol by distillation under reduced pressure (20 mm of mercury) and then extracts successively with 500 mls, 300 mls and 200 mls of methylene chloride. The combined organic phases are washed with 500 mls of water and then 500 mls of a saturated solution of sodium bicarbonate, dried over magnesium sulphate and evaporated to dryness under reduced pressure (20 mm of mercury). The residue (58 g) is chromatographed over 1 kg of silica gel contained in a column with a diameter of 6 cm, collecting fractions of 500 mls and eluting with ethyl acetate containing 1.5% of methanol. Fractions 31 to 43 are combined and evaporated to dryness. In this way one obtains 17 g of 1-[2(5,6-dimethoxy-3-indolyl) ethyl]-2-piperidone in the form of a thick yellow oil which slowly crystallises.

EXAMPLE 12

One heats 570 mls. of ethanol to 60° C. and then one adds 5.85 g of 10-chloro-2,3,4,6,7,12-hexahydro [2,3-a]-indolo-quinolizine.

One obtains a homogeneous solution to which one adds in one go 15.2 mls. of 30% aqueous formaldehyde solution.

The reaction mixture is maintained for 10 minutes at 60° C. and then one adds over a period of 1 minute 3.85 mls. of a 70% aqueous solution of perchloric acid. After cooling to 20° C., one adds with agitation, in small portions over a period of 15 minutes, 4.9 g of sodium borohydride. The excess of borohydride is destroyed by the addition of 290 mls. of a 1.25 M aqueous solution of sodium chloride. The agitation is continued for 20 minutes and then one extracts twice with 500 mls. of dichloromethane.

The combined organic phases are washed with twice 200 mls. of a 5 M sodium chloride solution and then dried over magnesium sulphate in the presence of bleaching charcoal, filtered, then concentrated to dryness under reduced pressure.

The product obtained (6.8 g) is agitated in a mixture of 20 mls. of methanol and 40 mls. of di-isopropyl oxide at 20° C.

By filtration one obtains 4.0 g of a pale yellow crystalline powder melting at 207° C., which is chromatographed over a column of 30 g of silica gel contained in a column of 2 cms. in diameter, collecting fractions of 30 mls. and eluting with a mixture of dichloromethane/methanol (97:3 by volume).

Fractions 3 to 8 are combined and evaporated.

The residue of 2.93 g is recrystallised from 600 mls. of di-isopropyl oxide.

One obtains in this way 1.9 g of 1,12b-trans-10-chloro-1,12-methanoxymethano-1,2,3,4,6,7,12,12b-octahydro-[2,3-a]-indolo-quinolizine in the form of fine white needles melting at 209° C.

Analysis: Calculated: C%, 67.43; H%, 6.33; Cl%, 11.71; N%, 9.25; O%, 5.28. Found: C%, 66.4; H%, 6.4; Cl%, 11.7; N%, 9.5; O%, 5.5.

10-chloro-2,3,4,6,7,12-hexahydro-[2,3-a]-indolo-quinolizine may be prepared in the following manner:

One brings into suspension 15 g of 1-[2(6-chloro-3-indolyl)-ethyl]-2-piperidone in 700 mls. of toluene and over a period of 5 minutes one adds a solution of 14 mls. of phosphorus oxychloride in 50 mls. of toluene.

The reaction mixture is then heated for 3 hours at 80° C. One adds 325 mls. of distilled water and continues the heating to 80° C. for a further 1 hour. After 16 hours at 4° C., the crystals are separated by filtration.

One obtains in this way 14 g of 10-chloro-1,2,3,4,6,7,12H-hexahydro-[2,3a]-indolo-quinolizinium chloride.

The chloride thus obtained is dissolved in 1000 mls. of distilled water at 35° C.

After cooling to 20° C. one adds, drop by drop, 60 mls. of 1 N soda.

The yellow precipitate obtained is separated by filtration, washed with water until neutral and then dried.

One obtains in this way 11.2 g of 10-chloro-2,3,4,6,7,12-hexahydro-[2,3-a]-indolo-quinolizine in the form of a yellow amorphous powder, which is used without any subsequent purification.

1-[2(6-chloro-3-indolyl)-ethyl]-2-piperidone may be prepared in the following manner:

One heats under a reflux under an atmosphere of nitrogen 22g of 6-chloro-tryptamine in 500 mls. of 2-methoxy-ethanol containing in suspension 12 g of anhydrous sodium carbonate.

Whilst maintaining the agitation and the heating under a reflux one adds over a period of 48 hours a solution of 23.65 g of ethyl 5-bromovalerianate in 200 mls. of 2-methoxy-ethanol.

When the addition is completed, one maintains the agitation and the heating under a reflux for a further 15 hours.

After cooling to 20° C. the mineral salts are separated by filtration and the filtrate is concentrated to dryness under reduced pressure (15 mm of mercury). One obtains a brown oil to which one adds 500 mls. of water. It is acidified to a pH of 1 by the addition of 4 N hydrochloric acid and then one extracts four times with 500 mls. of dichloromethane.

The combined organic phases are washed with twice 500 mls. of N hydrochloric acid, four times 500 mls. of distilled water, and then dried over magnesium sulphate and finally concentrated to dryness under reduced pressure.

One obtains 31.5 g of a brown oil which is chromatographed over a column of 150 g of silica gel contained in a column with a diameter of 3.5 cms, collecting fractions of 1000 mls. and eluting with a mixture of ethyl acetate and cyclohexane (35–65 by volume). Fractions 4 to 19 are combined and concentrated to dryness.

The residue of 22.5 g is recrystallised from ethyl acetate.

One obtains in this way 20.5 g of 1-[2(6-chloro-3-indolyl)-ethyl]-2-piperidone in the form of fine white needles which melt at 188° C. 6-chloro-tryptamine may be prepared according to F. Benington et al., J. Org. Chem., 25, 1542 (1960).

EXAMPLE 13

One heats 1800 mls. of ethanol to 60° C. and then one adds 18 g of 10-methyl-2,3,4,6,7,12-hexahydro-[2,3-a]-indolo-quinolizine.

One obtains a homogeneous solution to which one adds 44.5 mls. of 30% aqueous formaldehyde solution.

One maintains the reaction mixture agitated for 10 minutes at 60° C. and then one adds in a single go 11.2 mls. of 70% perchloric acid and cools immediately by means of a waterbath.

As soon as the temperature of the mixture reaches 21° C. one adds, in small portions, over a period of 15 minutes, 14 g of sodium borohydride. The agitation is continued for 30 minutes and then one adds 800 mls. of a 2.5 M sodium chloride solution and one agitates for 45 minutes until gas ceases to be evolved.

One then extracts with twice 400 mls. of dichloromethane.

The combined organic phases are washed with twice 200 mls. of water and then dried over magnesium sulphate, bleached over bleaching charcoal, filtered and finally concentrated to dryness.

One obtains 19 g of brown powder which is taken up again in 350 mls. of acetone under a reflux.

It is allowed to crystallise by cooling to 0° C. for 1 hour.

One obtains 7.5 g of yellow crystals.

By concentrating the filtrate to a small volume one obtains a second batch of 1.4 g under the same conditions.

The two batches are combined and chromatographed over a column of 117 g of silica gel contained in a column with a diameter of 3 cms., collecting fractions of 300 mls. and eluting with dichloromethane.

Fractions 3 to 11 are combined and evaporated.

The residue of 6.4 g is recrystallised from 240 mls. of acetone under a reflux.

One obtains in this way 6 g of 1,12b-trans-10-methyl-1,12-methanoxymethano-1,2,3,4,6,7,12,12b-octahydro-[2,3-a]-indolo-quinolizine in the form of fine white needles which melt at 178° C.

Analysis: Calculated: C%, 76.56; H%, 7.85; N%, 9.92; O%, 5.67. Found: C%, 75.6; H%, 8.0; N%, 9.9; O%, 5.9.

10-methyl-2,3,4,6,7,12-hexahydro-[2,3-a]-indolo-quinolizine may be prepared in the following manner:

25 g of 1-[2(6-methyl-3-indolyl)-ethyl]-2-piperidone are suspended in 1200 mls. of toluene and over a period of 5 minutes one adds a solution of 25.3 mls. of phosphorus oxychloride in 50 mls. of toluene.

The reaction mixture is heated at 80° C. for 3 hours.

One adds 600 mls. of distilled water and continues the heating at 80° C. for a further 1 hour.

One cools to a temperature in the vicinity of 20° C. and then one adds a solution of 21 g of sodium perchlorate monohydrate in 270 mls. of water.

After 16 hours at a temperature in the vicinity of 4° C., the crystals are separated by filtration, washed with water and dried.

One obtains in this way 44.8 g of wet product containing 31 g of 10-methyl-1,2,3,4,6,7,12H-hexahydro-[2,3-a]-indolo-quinolizinium perchlorate.

The wet perchlorate is dissolved in 2 liters of methanol under a reflux. One adds 2 liters of distilled water and maintains the heating under a reflux.

It is then allowed to return to a temperature in the vicinity of 20° C. One obtains a clear yellow solution to which one adds 120 mls. of 1 N soda, whilst agitating vigorously.

After 30 minutes' agitation the solid product is separated by filtration and washed with water to neutrality.

After drying one obtains 18.8 g of 10-methyl-2,3,4,6,7,12-hexahydro-[2,3-a]-indolo-quinolizine in the form of a light yellow powder which is used without subsequent purification.

1-[2(6-methyl-3-indolyl)-ethyl]-2-piperidone may be prepared in the following manner:

One heats under a reflux under an atmosphere of nitrogen 21 g of 6-methyl-tryptamine in 500 mls. of methoxyethanol containing 12.84 g of anhydrous sodium carbonate in suspension.

Whilst maintaining the agitation and the heating under a reflux one adds over a period of 20 hours a solution of 25.3 g of ethyl 5-bromovalerianate in 130 mls. of 2-methoxyethanol. When the addition is completed, one maintains the agitation and the heating under a reflux for 15 hours.

It is then filtered at 20° C. and the filtrate is concentrated under reduced pressure (15 mm of mercury).

One obtains a brown oil to which one adds 400 mls. of water. It is acidified by the addition of 20 mls. of 4 N hydrochloric acid and extracted 4 times with 400 mls. of dichloromethane. The combined organic phases are washed successively with twice 500 mls. of N hydrochloric acid and 4 times 500 mls. distilled water, then dried over magnesium sulphate and finally concentrated to dryness under reduced pressure.

One obtains 28.8 g of a brown oil which is chromatographed over 140 g of silica contained in a column with a diameter of 3.5 cms., collecting fractions of 500 mls. and eluting with an ethyl acetate gradient in cyclohexane.

Fractions 14 to 50 eluted with a mixture of ethyl acetate/cyclohexane (1:1 by volume) are combined and concentrated to dryness under reduced pressure.

In this way one obtains 24.7 g of a solid melting at 140° C. which is recrystallized from 400 mls. of ethyl acetate. One obtains 23 g of 1-[2(6-methyl-3-indolyl)-ethyl]-2-piperidone in the form of fine silky needles melting at 154° C. and then 160° C.

6-methyltryptamine may be prepared according to J. H. GASSUM et al., Quat. J. Exp. Physiol., 40, 49 (1955).

EXAMPLE 14

One dissolves 1.5 g of the product obtained in Example 1 in the form of a base in 200 mls. of hot methanol. One then adds 1.13 g of (1)-di-O,O'-paratoluoyl tartaric acid in 20 mls. of hot methanol. After standing for 14 hours at a temperature in the vicinity of 20° C., the salt is separated by ciltration and then recrystallised from 400 mls. of a mixture of dioxan/methanol (75:25 by volume). After 14 hours' standing at a temperature in the vicinity of 20° C. one obtains 1.36 g of salt which, after alkalisation and extraction provides 0.57 g of base, which is purified by chromatography over 15 g of silica in chloroform, eluting with a mixture of chloroform/methanol (98:2 by volume).

One obtains in this way 0.47 g of (1)-1,12b-trans-1,2,3,4,6,7,12,12b-octahydro-1,12-methanoxymethano-[2,3-a]-indolo-quinolizine:

$$[\alpha]_D^{-°} = -127° \ (c = 1, \text{chloroform})$$

EXAMPLE 15

Operating as in example 14 but starting off from 1.42 g of base and 1.07 g of (d)-di-O,O'-paratoluoyl tartaric acid, one obtains 0.355 g of (d)-1,12b-trans-1,2,3,4,6,7,12,12b-octahydro-1,12-methanoxymethano-[2,3-a]-indolo-quinolizine:

$$[\alpha]_D^{20} = +124° \ (c = 1, \text{chloroform})$$

The pharmaceutical compositions containing a product of the general formula (I) and/or one of its salts in the pure state or in the presence of a diluent or of a casing constitute another object of the present invention. These compositions may be used per os, rectally or parenterally.

As solid compositions for oral administration one may use tablets, pills, powders or granules. In these compositions, the active product according to the invention is mixed with one or more inert diluents such as saccharose, lactose or starch. These compositions may also include substances other than diluents, for example wetting agents, sweetening agents or flavourings.

The compositions according to the invention for parenteral administration may be aqueous or non-aqueous sterile solutions, suspensions or emulsions. As solvent or vehicle one may use propyleneglycol, polyethyleneglycol, vegetable oils, particularly olive oil, injectable organic esters, for example ethyl oleate. These compositions may also contain adjuvants, paticularly wetting agents, emulsifiers or dispersants. The sterilisation may be carried out in a number of way, for example by means of a bacteriological filter, incorporating sterilising agents in the composition, by irradiation or by heating. They may also be prepared in the form of sterile solid compositions which can be dissolved at the moment of use in sterile water or any other injectable sterile medium.

The compositions for rectal administration are suppositories which may contain, in addition to the active product, excipients such as cocoa butter or suppository wax.

In human therapy, the compositions according to the invention are particularly useful in the treatment of cerebro-vascular accidents and functional disorders of cerebral circulatory insufficiency, in the treatment of arteriopathies of the limbs and circulatory troubles of the extremities.

The doses to be used depend on the effect aimed at and the duration of the treatment. They are generally between 25 and 500 mg per day by oral route for an adult, by intramuscular route they may be between 20 and 50 mg per day and by intravenous route, in slow perfusion, they may be between 10 and 30 mg per day.

Generally speaking, the physician will determine the dosage which he deems most appropriate, according to the age, weight and all the other factors connected with the patient to be treated.

EXAMPLE 16

One prepares according to the usual technique tablets containing 25 mg of active product having the following composition:

| | |
|---|---|
| 1,12b-trans-1,2,3,4,6,7,12,12b-octahydro-1,12-methanooxymethano-2,3-a-indolo-quinolizine | 0.025 g |
| starch | 0.090 g |
| precipitated silica | 0.030 g |
| magnesium stearate | 0.005 g |

What is claimed is:

1. A pentacyclic derivative of the general formula:

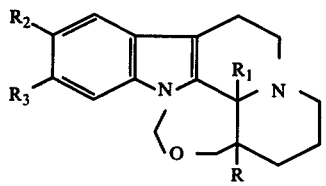

in which:

$R$ represents a hydrogen atom or a hydroxymethyl radical, $R_1$ represents a hydrogen atom, $R$ and $R_1$ being in the trans position in relation to one another, and $R_2$ and $R_3$, which may be the same or different, represent a hydrogen atom or a halogen atom or an alkyl radical containing 1 to 4 carbon atoms or alkyloxyl radical whose alkyl part contains 1 to 4 carbon atoms, or else $R_2$ and $R_3$ together form a dioxymethylene radical, its optically active forms, its pharmaceutically acceptable addition salts with acids, its pharmaceutically acceptable quaternary ammonium salts and its N-oxides.

2. 1,12b-trans-1,2,3,4,6,7,12,12b-octahydro-1,12-methanooxymethano [2,3-a]-indolo-quinolizine, its pharmaceutically acceptable salts and its optically active forms.

3. A process for the preparation of a product in accordance with claim 1, which comprises reacting formaldehyde with a compound of the formula:

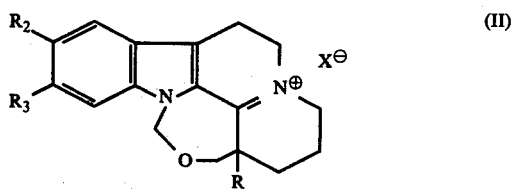

and salifying the product obtained by means of an acid to obtain an immonium salt of the formula:

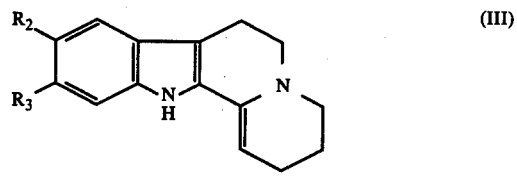

and reducing the latter in an acid medium to obtain a compound of the formula I: $R$, $R_2$ and $R_3$ being defined as in claim 1 and X being an anion.

4. A vasodilating composition for use in Human therapy, comprising an effective vasodilating amount of a product according to claim 1 in association with one or more diluents or adjuvants which are compatible with the product and pharmaceutically acceptable.

* * * * *